US012427295B2

(12) United States Patent
Isaacson

(10) Patent No.: US 12,427,295 B2
(45) Date of Patent: Sep. 30, 2025

(54) CATHETER FLUSH DEVICE, SYSTEM, AND METHODS

(71) Applicant: Becton, Dickinson and Company, Franklin Lakes, NJ (US)

(72) Inventor: S. Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1071 days.

(21) Appl. No.: 16/741,998

(22) Filed: Jan. 14, 2020

(65) Prior Publication Data

US 2020/0246603 A1     Aug. 6, 2020

Related U.S. Application Data

(60) Provisional application No. 62/799,211, filed on Jan. 31, 2019.

(51) Int. Cl.
*A61M 39/02*       (2006.01)
*A61M 5/142*       (2006.01)
(Continued)

(52) U.S. Cl.
CPC ........ *A61M 39/0247* (2013.01); *A61M 5/142* (2013.01); *A61M 5/16831* (2013.01);
(Continued)

(58) Field of Classification Search
CPC ...... A61M 39/0247; A61M 2005/1403; A61M 2025/0019; A61M 2039/0018;
(Continued)

(56) References Cited

U.S. PATENT DOCUMENTS 3,908,657 A * 9/1975 Kowarski ........ A61B 5/150267
600/580
4,150,672 A * 4/1979 Whitney ............. A61M 5/1422
604/246
(Continued)

FOREIGN PATENT DOCUMENTS

EP          2646070 B1 *  1/2015  .......... A61M 5/1408
JP       2013544161 A    12/2013
(Continued)

*Primary Examiner* — Bhisma Mehta
*Assistant Examiner* — Fatimata Sahra Diop
(74) *Attorney, Agent, or Firm* — Kirton McConkie; Whitney Blair; Kevin Stinger

(57) ABSTRACT

A flush device may be used to flush a catheter system. The flush device may include a housing, a proximal connector coupled to the housing, and a distal connector coupled to the housing. The flush device may include a first conduit disposed within the housing and extending between the proximal connector and the distal connector. The flush device may include a second conduit disposed within the housing and in fluid communication with the first conduit. The flush device may include a fluid reservoir, which may be disposed within the housing of the flush device. The flush device may include a pump that pumps fluid from the fluid reservoir, through the second conduit, and into the first conduit. The device may include a one-way valve, which may prevent fluid from flowing beyond the one-way valve toward the fluid reservoir.

15 Claims, 7 Drawing Sheets

(51) Int. Cl.
 *A61M 5/168* (2006.01)
 *A61M 25/00* (2006.01)
 *A61M 5/14* (2006.01)
 *A61M 39/00* (2006.01)

(52) U.S. Cl.
 CPC ..... *A61M 25/00* (2013.01); *A61M 2005/1403* (2013.01); *A61M 2025/0019* (2013.01); *A61M 2039/0018* (2013.01); *A61M 2039/0258* (2013.01); *A61M 2039/027* (2013.01)

(58) Field of Classification Search
 CPC .. A61M 2005/1404; A61M 2039/0258; A61M 5/168; A61M 2005/1402; A61M 1/77–744; A61B 5/150992
 See application file for complete search history.

(56) References Cited

U.S. PATENT DOCUMENTS

| | | | | |
|---|---|---|---|---|
| 4,657,486 | A * | 4/1987 | Stempfle | F04B 49/02 604/153 |
| 5,482,446 | A * | 1/1996 | Williamson | F04B 43/082 417/474 |
| 5,957,898 | A * | 9/1999 | Jepson | A61M 39/045 604/533 |
| 6,102,897 | A | 8/2000 | Volker | |
| 8,066,670 | B2 | 11/2011 | Cluff et al. | |
| 2004/0039344 | A1* | 2/2004 | Baldwin | A61M 5/1454 604/209 |
| 2004/0186408 | A1* | 9/2004 | Behague | A61B 5/154 604/4.01 |
| 2010/0179489 | A1* | 7/2010 | Harding | A61M 39/045 604/535 |
| 2012/0035471 | A1 | 2/2012 | Lee-Sepsick et al. | |
| 2012/0209190 | A1 | 8/2012 | Gray et al. | |
| 2014/0121591 | A1 | 5/2014 | Kissinger | |
| 2014/0188002 | A1* | 7/2014 | Close | A61M 5/16804 600/581 |
| 2014/0276411 | A1 | 9/2014 | Cowan et al. | |
| 2018/0259420 | A1* | 9/2018 | Rule | A61B 5/15003 |

FOREIGN PATENT DOCUMENTS

| | | |
|---|---|---|
| JP | 7466554 B2 | 4/2024 |
| KR | 20180028877 A | 3/2018 |
| KR | 20220157453 A | 11/2022 |
| WO | 2009/044221 | 4/2009 |
| WO | 2012/126745 | 2/2012 |

* cited by examiner

CATHETER FLUSH DEVICE, SYSTEM, AND METHODS

RELATED APPLICATIONS

This application claims the benefit of U.S. Provisional Application No. 62/799,211, filed on Jan. 31, 2019, entitled "CATHETER FLUSH DEVICE, SYSTEM, AND METHODS," which is incorporated herein in its entirety.

BACKGROUND

Infusion therapy, a common healthcare procedure, may be facilitated by a vascular access device. Hospitalized, home care, and other patients receive fluids, pharmaceuticals, and blood products via a vascular access device inserted into the vascular system. Blood withdrawal is another common healthcare procedure that may be facilitated by a vascular access device.

A vascular access device may access a peripheral or central vasculature of a patient. A vascular access device may be indwelling for short term (days), moderate term (weeks), or long term (months to years). A vascular access device may be used for continuous infusion therapy or for periodic infusion therapy. A common type of vascular access device is a catheter, such as, for example, a peripheral intravenous catheter (PIVC) or a peripherally inserted central catheter (PICC).

When a catheter remains in the vasculature of the patient for a prolonged period of time, the catheter may be more susceptible to an occlusion or blockage by debris (e.g., fibrin or platelet clots). A catheter occlusion can lead to catheter infection, pulmonary embolism, post-thrombotic syndrome, and other negative health outcomes. When an occlusion in a catheter occurs, the catheter may be removed and/or replaced, which may result in an additional needle stick, pain to the patient, and higher material costs.

Current occlusion prevention measures include manually flushing the catheter, but adherence to flushing protocols may vary across clinicians. In some instances, a thrombolytic agent may be used to break up the occlusion in the catheter. However, the thrombolytic agent is often expensive and installation of the thrombolytic agent may interrupt infusion therapy through the catheter. Further, risk of occlusion of the catheter may lead to increased manual flushing, which may result in an increased risk of infection.

The subject matter claimed herein is not limited to embodiments that solve any disadvantages or that operate only in environments such as those described above. Rather, this background is only provided to illustrate one example technology area where some implementations described herein may be practiced.

SUMMARY OF THE INVENTION

The present disclosure relates generally to devices, systems, and methods to reduce or eliminate catheter occlusions. In some embodiments, a flush device may facilitate automatic flushing of a catheter to reduce or eliminate occlusion of the catheter. In some embodiments, the flush device may be portable and configured to facilitate performance of multiple tasks by a clinician. In some embodiments, the flush device may facilitate one or more of the following: manual flushing of the catheter, connection to an IV line, and blood collection.

In some embodiments, the flush device may include a housing. In some embodiments, the flush device may include a proximal connector coupled to the housing and/or a distal connector coupled to the housing. In some embodiments, the flush device may include a first conduit disposed within the housing and extending between the proximal connector and the distal connector. In some embodiments, the flush device may include a second conduit disposed within the housing and in fluid communication with the first conduit.

In some embodiments, the flush device may include a fluid reservoir disposed within the housing. In some embodiments, the fluid reservoir may be external to the housing. In some embodiments, the second conduit may extend between the first conduit and the reservoir. In some embodiments, the flush device may include a pump disposed within the housing. In some embodiments, the pump may be configured to pump fluid from the fluid reservoir, through the second conduit, and into the first conduit. In some embodiments, the flush device may include a one-way valve disposed within the second conduit. In some embodiments, the one-way valve may be configured to prevent fluid from flowing beyond the one-way valve toward the fluid reservoir.

In some embodiments, the distal connector may be configured to couple to a vascular access device. In some embodiments, the proximal connector may include a needleless connector. In some embodiments, the proximal connector may be integrally formed with the housing. In some embodiments, the flush device may be coupled to a clothing article to be worn by a patient. In some embodiments, the clothing article may be configured to secure the housing of the flush device to the patient.

In some embodiments, the flush device may include a container. In some embodiments, the fluid reservoir may be disposed within the container. In some embodiments, the container may be removably disposed within the housing. In some embodiments, the container may be removed from the housing or installed into the housing by a clinician. In some embodiments, the fluid reservoir may include a vial, which may contain a fluid, such as, for example, saline. In some embodiments, the vial may hold about 5 mL of the fluid. In some embodiments, the vial may hold more than 5 mL or less than 5 mL of the fluid.

In some embodiments, the pump may include an electric pump, which may provide a fluid flow rate of about 0.2 mL/hr. In these and other embodiments, the pump may facilitate continuous or periodic flushing of the catheter, which may prevent occlusion. In some embodiments, the pump may facilitate continuous flushing of the catheter during activation of the pump.

In some embodiments, a method may include coupling a vascular access device to the flush device and activating the pump of the flush device to provide fluid from the fluid reservoir to the first conduit. In some embodiments, the fluid may be pumped from the fluid reservoir to the second conduit. In some embodiments, after the fluid flows through the second conduit, the fluid may flow distally through the first conduit and into the vascular access device.

In some embodiments, the fluid reservoir may be depleted. In some embodiments, the method may include replacing the fluid reservoir with another fluid reservoir after deactivating the pump. In some embodiments, replacing the fluid reservoir with the other fluid reservoir may include decoupling the fluid reservoir from the second conduit, and coupling the other fluid reservoir to the second conduit. In some embodiments, the fluid reservoir may contain less fluid compared to the other fluid reservoir. In some embodiments, the method may include activating the pump, which may be performed in response to replacement of the fluid reservoir with the other fluid reservoir. In some embodiments, the other reservoir may include another container, such as, for example, a vial.

In some embodiments, the method may include securing the flush device to the patient. In some embodiments, the flush device may be secured to the patient via the clothing article, such as, for example, an arm band or another suitable clothing article. In some embodiments, one or more of the following may be performed when the flush device is secured to the patient: infusing fluid to the patient via the pump, coupling an IV line to the proximal connector, coupling a blood collection device to the proximal connector, and coupling a syringe to the proximal connector. In some embodiments, the flush device may not be removed from the patient (for example, the clothing article or arm band may remain secured to the patient) in between one or more of the following: infusing fluid to the patient via the pump, coupling the IV line to the proximal connector, coupling the blood collection device to the proximal connector, and coupling the syringe to the proximal connector.

In some embodiments, a method of aspirating blood from the patient may include coupling the vascular access device to the flush device, deactivating the pump, coupling a blood collection device to the proximal connector, and extracting a blood sample through the proximal connector into the blood collection device. In some embodiments, the method of aspirating blood from the patient may include coupling a syringe to the proximal connector of the flush device and manually flushing the first conduit via the syringe. In some embodiments, in response to extracting the blood sample through the proximal connector into the blood collection device and uncoupling the blood collection device from the proximal connector, the syringe may be coupled to the proximal connector and the first conduit may be manually flushed.

It is to be understood that both the foregoing general description and the following detailed description are examples and explanatory and are not restrictive. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF THE DRAWINGS

Example embodiments will be described and explained with additional specificity and detail through the use of the accompanying drawings in which.

DESCRIPTION OF EMBODIMENTS

Figure 1:
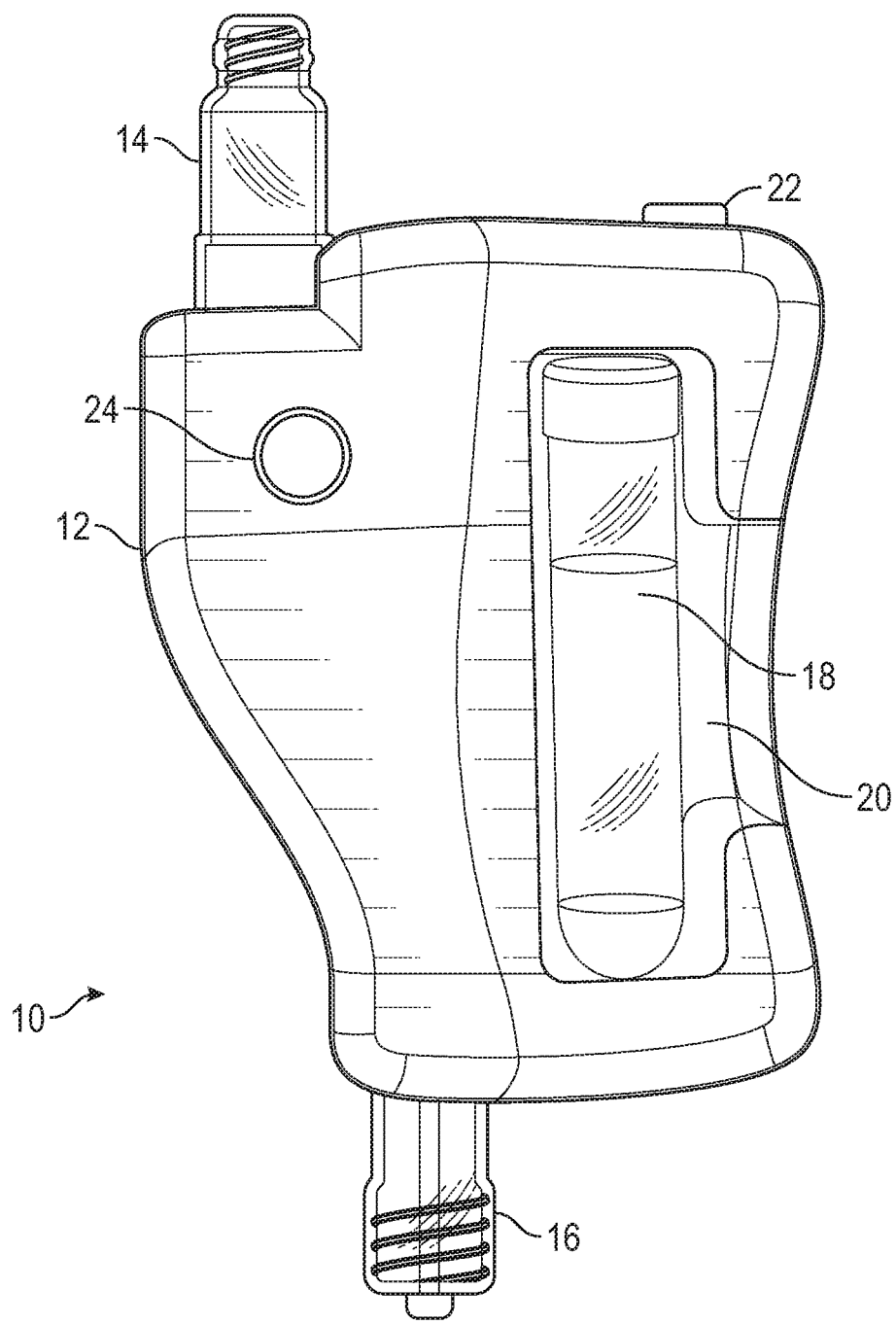
FIG. 1 is an upper perspective view of an example flush device, according to some embodiments.

The present disclosure relates generally to devices, systems, and methods to reduce or eliminate catheter occlusions. Referring now to FIG. 1, in some embodiments, a flush device 10 may include a housing 12. In some embodiments, the flush device 10 may include a proximal connector 14 coupled to the housing 12, and a distal connector 16 coupled to the housing 12. In some embodiments, the proximal connector 14 and/or the distal connector 16 may be integrally formed with the housing 12. In some embodiments, the proximal connector 14 may include a needleless connector.

In some embodiments, the flush device 10 may include a fluid reservoir 18, which may be disposed within a container 20. In some embodiments, the container 20 may include a vial, syringe, or another suitable container. In some embodiments, the flush device 10 may include a pump disposed within the housing 12.

In some embodiments, the pump may include an operation switch 22, which may be used to activate and/or deactivate the pump. In some embodiments, the operation switch 22 and/or an indicator 24 may be disposed on the housing 12 so as to be visible to the clinician. In some embodiments, the operation switch 22 may include a push button or another suitable switch.

In some embodiments, a state of operation of the pump, such as, for example, activated or deactivated, may be shown by the indicator 24, which may include a light or other suitable indicator. In some embodiments, the indicator 24 may be electrically coupled with one or more other devices. In some embodiments, the indicator 24 may provide information to the clinician. In some embodiments, the information may include one or more of the following: battery life, fluid flow rate, and fluid volume remaining in the fluid reservoir 18.

Figure 2A:
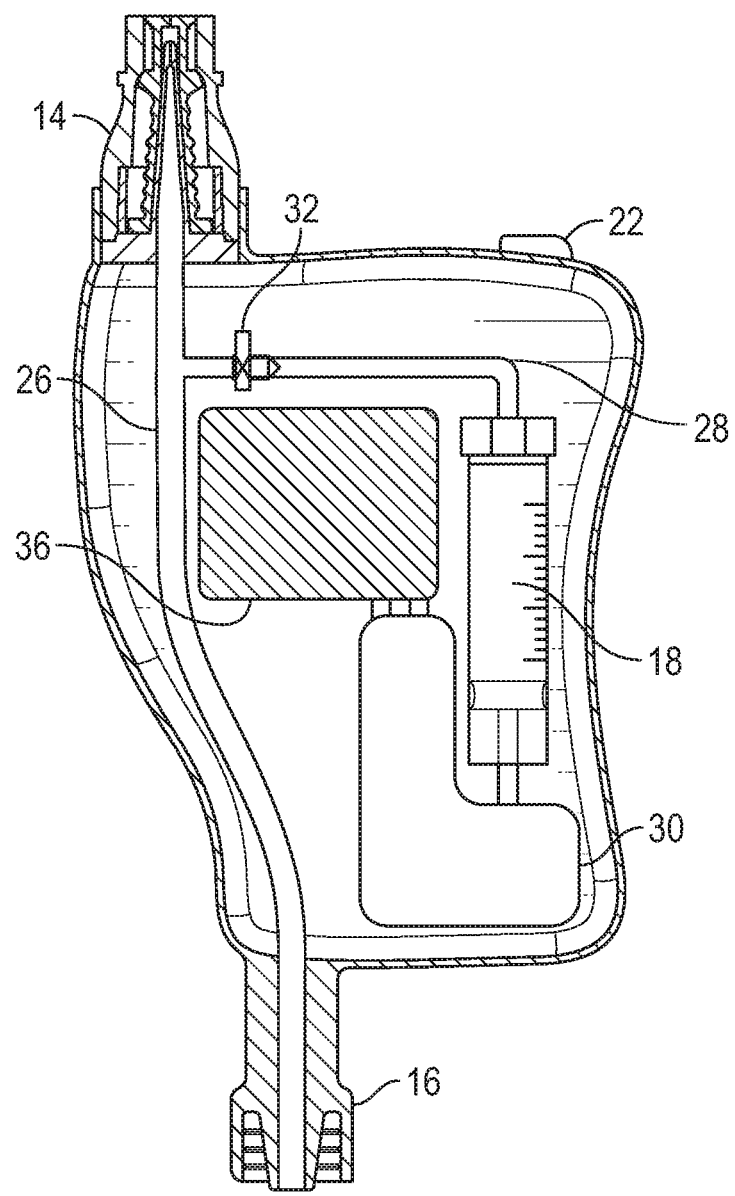
FIG. 2A is a cross-sectional view of the flush device of FIG. 1, illustrating an example first conduit, an example second conduit in fluid communication with the first conduit, and an example pump according to some embodiments.

Referring now to FIG. 2A, in some embodiments, the flush device 10 may include a first conduit 26 disposed within the housing 12 and extending between the proximal connector 14 and the distal connector 16. In some embodiments, the first conduit 26 may include tubing or may be integrally formed with the housing 12. In some embodiments, the tubing may be flexible. In some embodiments, a second conduit 28 may also be disposed within the housing 12 and in fluid communication with the first conduit 26.

In some embodiments, the second conduit 28 may extend between the first conduit 26 and the fluid reservoir 18. In some embodiments, the second conduit 28 may include tubing or may be integrally formed with the housing 12. In some embodiments, the second conduit 28 may intersect with the first conduit 26. In some embodiments, the second conduit 28 may be coupled to the first conduit 26 via a T-connector or another suitable connector.

In some embodiments, the flush device 10 may include the pump 30, which may be disposed within the housing 12. In some embodiments, the pump 30 may be configured to pump fluid from the fluid reservoir 18, through the second conduit 28, and into the first conduit 26. In some embodiments, the fluid may include saline or another fluid. In some embodiments, the fluid pumped by the pump 30 may reach the vascular access device to facilitate prevention of occlusion of the vascular access device.

In some embodiments, the pump 30 may provide a fluid flow rate, which may be about 0.2 mL/hr. In some embodiments, the fluid flow rate may be greater than about 0.2 mL/hr. In some embodiments, the fluid flow rate may be between about 0.2 mL/hr and about 0.5 mL/hr. In some embodiments, the fluid flow rate may be between about 0.2 mL/hr and about 1 mL/hr. In these and other embodiments, the pump 30 may pump the fluid continuously or periodically to flush the vascular access device. In some embodiments, the pump 30 may provide continuous or periodic automatic flushing of the vascular access device in response to activation of the pump 30. In some embodiments, the continuous or periodic automatic flushing may occur until the pump 30 is deactivated.

In some embodiments, the pump 30 may include any type of suitable pump known in the art. In some embodiments, the pump 30 may include a peristaltic medical infusion pump, a rotary piston pump, a syringe or syringe pump, a piston brake pump, or any other suitable pump. In some embodiments, the pump 30 may be electric. In some embodiments, the pump 30 may be electrically coupled to a power supply 36. In some embodiments, the power supply 36 may be located internal to the housing 12 of flush device 10. In some embodiments, the power supply 36 may include an alkaline battery. In some embodiments, the power supply 36 may include a rechargeable battery, external power supply or another suitable power source. It is understood that a location of the power supply 36, as well as other features, within the housing 12 may vary.

In some embodiments, the pump 30 and/or elastomeric forces may provide a constant or consistent pressure on the fluid reservoir 18. In some embodiments, the elastomeric forces on the fluid reservoir 18 may be provided by a manual pressure adjustment, such as, for example, a handle or twisting dial operated from outside the housing 12.

In some embodiments, the pump 30 may include a solenoid valve that may be activated by the pump 30 to allow fluid to flow through the second conduit 28. In some embodiments, the solenoid valve may be maintained in a closed position when a magnetic solenoid is not energized. In some embodiments, when the magnetic solenoid is energized, the solenoid valve may open allowing fluid to flow from the fluid reservoir 18 through the second conduit 28.

In some embodiments, the container 20 may be removably disposed within the housing 12. In some embodiments, the housing 12 may be configured to have an access door so that the container 20 may be installed or removed into flush device 10. In some embodiments, the fluid reservoir 18 may include a vial, which may contain saline or another fluid. In some embodiments, the fluid reservoir 18 may include between about 2 mL and about 10 mL of fluid. In some embodiments, the fluid reservoir 18 may include about 5 mL of fluid. In some embodiments, the fluid reservoir 18 may include more than about 10 mL of fluid.

In some embodiments, the fluid reservoir 18 may be external to the housing 12. In some embodiments, the fluid reservoir 18 may include a syringe or another suitable fluid reservoir. In some embodiments, the fluid reservoir 18 is a first fluid reservoir that may be replaced or replenished. In some embodiments, the first fluid reservoir may have less fluid compared to a second fluid reservoir. In some embodiments, the replacing of the fluid reservoir 18 after deactivating the pump 30 may include decoupling the first fluid reservoir 18 from the second conduit 28, coupling the second fluid reservoir to the second conduit 28, and then activating the pump 30.

In some embodiments, the flush device 10 may include a one-way valve 32 disposed within the second conduit 28. In some embodiments, the one-way valve 32 may be configured to prevent fluid from flowing beyond the one-way valve 32 and toward the fluid reservoir 18. In some embodiments, the one-way valve 32 may include a check valve. In some embodiments, the one-way valve 32 may prevent fluid, such as, for example, medication or blood, from entering into the pump 30 and/or the fluid reservoir 18.

Figure 2B:
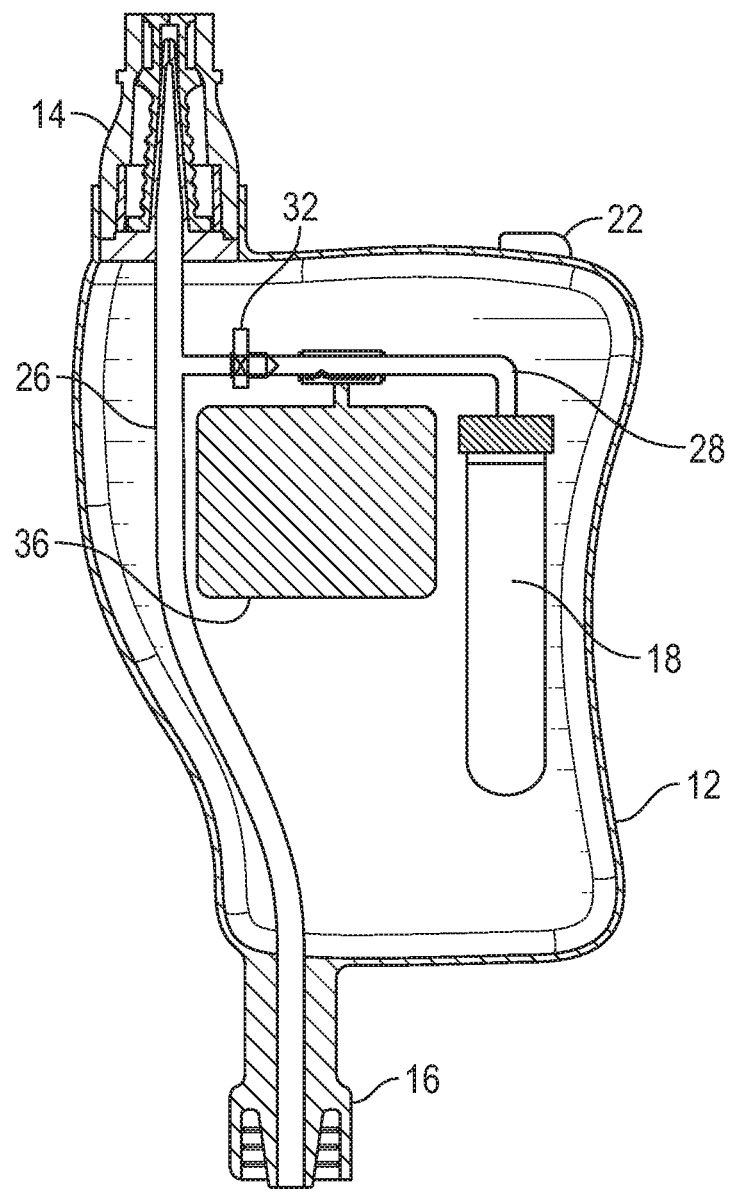
FIG. 2B is another cross-sectional view of the flush device of FIG. 1, illustrating the first conduit, the second conduit in fluid communication with the first conduit, and another example pump, according to some embodiments.
Figure 2C:
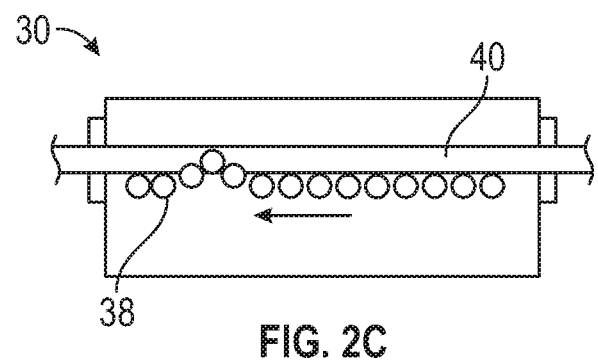
FIG. 2C is an enlarged view of the pump of FIG. 2B, according to some embodiments.

Referring now to FIG. 2B-2C, in some embodiments, the pump 30 may include a peristaltic medical infusion pump. In some embodiments, the second conduit 28 may be formed by the tubing 40. In some embodiments, the pump 30 may include members 38 that sequentially push on the tubing 40 and force the fluid to flow in a lateral direction and/or towards the first conduit 26. In some embodiments, the pump 30 may operate intermittently or periodically. In some embodiments, the pump 30 may provide episodic bursts of fluid at a regular interval and/or throughout a given time period.

Figure 3B:
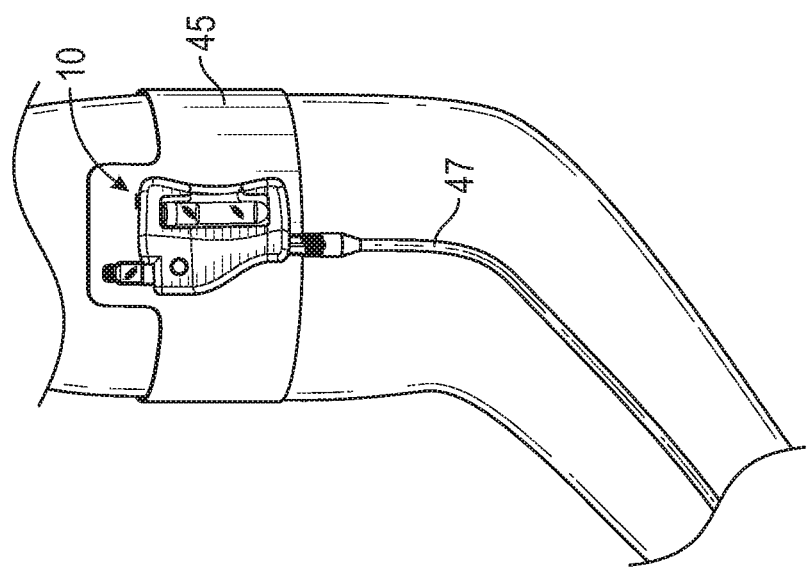
FIG. 3B is an upper perspective view of the flush device of FIG. 1 coupled to a an example clothing article worn by a patient, according to some embodiments.
Figure 3A:
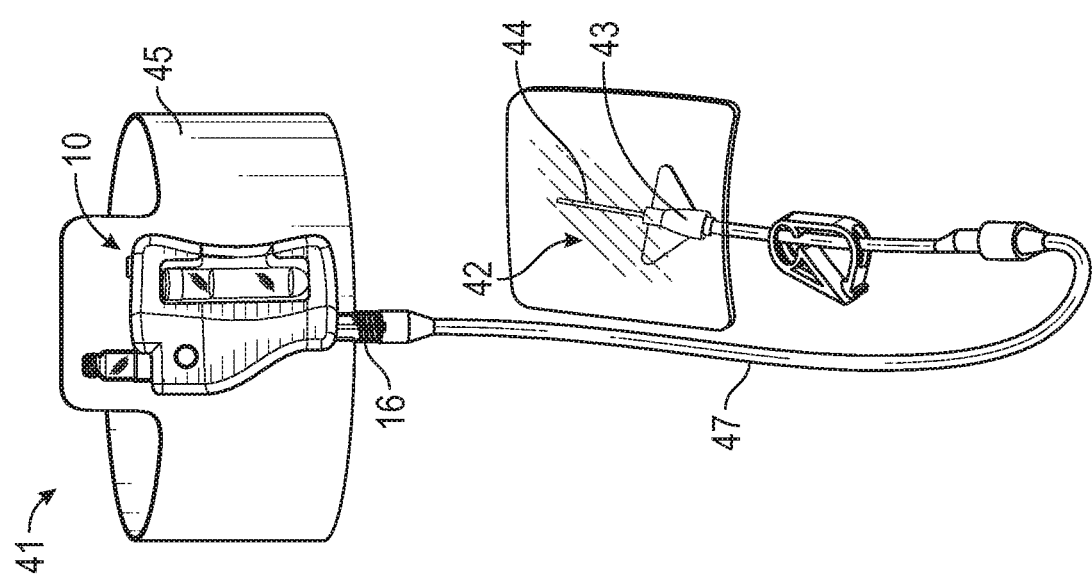
FIG. 3A is an upper perspective view of an example catheter system that includes the flush device of FIG. 1, according to some embodiments.

Referring now to FIG. 3A, a catheter system 41 is illustrated, according to some embodiments. In some embodiments, the flush device 10 may be coupled to a vascular access device 42 or another suitable device. In further detail, an extension tube 47 may be coupled to the distal connector 16 and may extend between the vascular access device 42 and the flush device 10.

In some embodiments, the vascular access device 42 may include a catheter adapter 43. In some embodiments, the catheter adapter 43 may include a proximal end, a distal end, and a lumen extending therebetween. In some embodiments, the catheter adapter 43 may include a catheter 44 extending from the distal end. In some embodiments, the catheter 44 may include a PIVC or a PICC.

In some embodiments, the distal connector 16 may be integrally formed with the housing 12. In some embodiments, the distal connector 16 may include a luer adapter, such as a slip or thread male or female luer adapter, or another suitable connector. In some embodiments, a proximal end of the extension tube 47 may be integrally formed with the distal connector 16.

Referring now to FIGS. 3A-3B, in some embodiments, the flush device 10 may be coupled to a clothing article 45 configured to be worn by a patient. In some embodiments, the housing 12 may be coupled to the clothing article 45 via threads, snaps, adhesive, or any other suitable coupling mechanism. In some embodiments, the clothing article 45 may secure the housing 12 to the patient. In one embodiment, the clothing article 45 may be an armband that may be secured to the arm of a person, as illustrated, for example, in FIG. 3B. In some embodiments, the clothing article 45 may include a gown, a wrap, or another suitable clothing article. In some embodiments, the catheter system 41 may not include the clothing article 45.

Figure 4A:
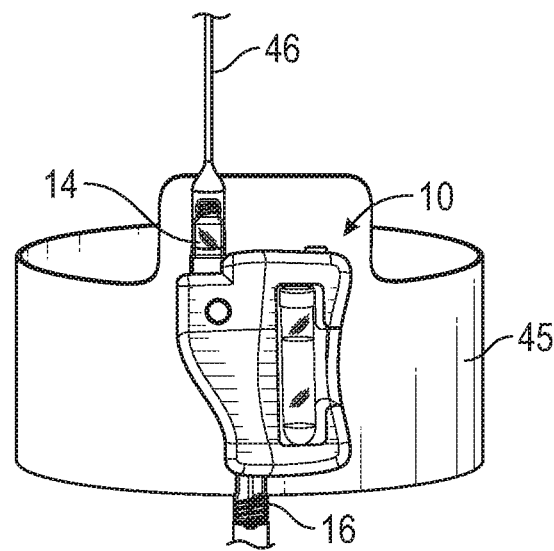
FIG. 4A is an upper perspective view of the flush device of FIG. 1 coupled to an example intravenous (IV) line, according to some embodiments.

Referring now to FIG. 4A, in some embodiments, the proximal connector 14 may be configured to couple to an intravenous (IV) line 46. In some embodiments, fluid from the IV line 46 may pass through the first conduit 26 and into the vascular access device 42. In some embodiments, the proximal connector 14 may be coupled to one or more alternate fluid sources as required by an operator of the flush device 10. In some embodiments, the proximal connector 14 may include a needleless connector or another suitable connector. In some embodiments, the proximal connector 14 may be configured to couple to a fluid supply, such as the IV line 46.

Figure 4B:
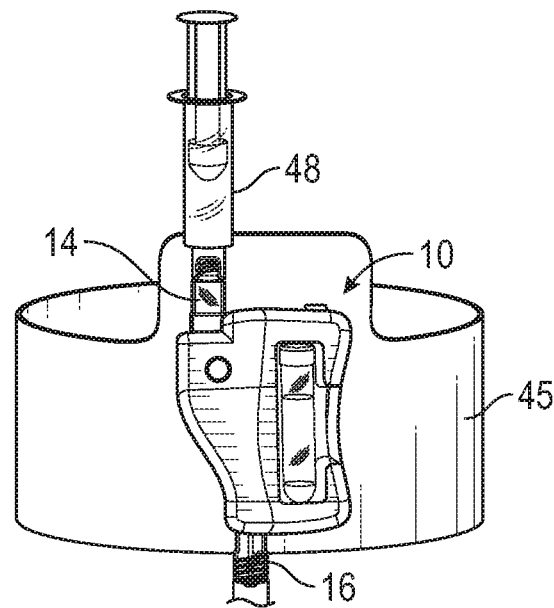
FIG. 4B is an upper perspective view of the flush device of FIG. 1 coupled to an example syringe, according to some embodiments.

Referring to FIG. 4B, in some embodiments, a syringe 48 may be coupled to the proximal connector 14 of the device. In some embodiments, the syringe 48 may contain fluid, such as, for example, medicine to administer to the patient through the flush device 10 or saline to flush the flush device 10 and/or the vascular access device 42. In some embodiments, when a particular fluid is administered by the IV line 46 (illustrated, for example, in FIG. 4A) or manually with the syringe 48, the one-way valve 32 (illustrated, for example, in FIGS. 2A-2B) may prevent the particular fluid from entering one or more of the following: the second conduit 28, the pump 30, and the fluid reservoir 18. In some embodiments, the pump 30 may facilitate flushing of the flushing device 10 and/or the vascular access device 42 at multiple fluid flow rates. In further detail, in some embodiments, manual activation of the syringe 48 may facilitate flushing at a first fluid flow rate and activation of the pump 30 may facilitate flushing at a second fluid flow rate.

Figure 4C:
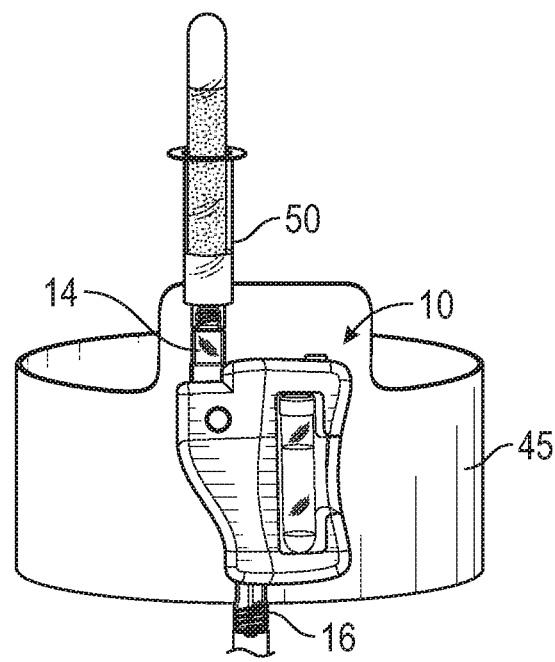
FIG. 4C is an upper perspective view of the flush device of FIG. 1 coupled to an example blood collection device, according to some embodiments.

Referring to FIG. 4C, in some embodiments, a blood collection device 50 may be coupled to the proximal connector 14. In some embodiments, a blood sample contained in the blood collection device 50 may be collected from the vascular access device 42 coupled to the flush device 10. In some embodiments, the blood sample may be drawn proximally through the first conduit 26 and out of the proximal connector 14 into the blood collection device 50 coupled to the proximal connector 14.

In some embodiments, the pump 30 may be deactivated prior to collection of the blood sample. In some embodiments, after the blood sample has been collected in the blood collection device 50, the clinician may uncouple the blood collection device 50 from the proximal connector 14 and couple the syringe 48 to the proximal connector 14. In some embodiments, the syringe 48 may be used to manually flush the first conduit 26 and/or the vascular access device 42. In some embodiments, when the blood sample is collected, the one-way valve 32 may prevent blood from entering one or more of the following: the second conduit 28, the pump 30, and the fluid reservoir 18.

Figure 4D:
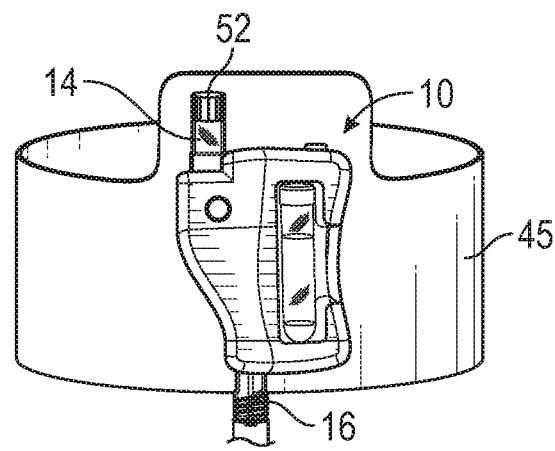
FIG. 4D is an upper perspective view of the flush device of FIG. 1, illustrating an example cap coupled to an example proximal connector, according to some embodiments.

Referring to FIG. 4D, in some embodiments, the proximal connector 14 and/or the distal connector 16 may each include a cap 52, which may be removable. In some embodiments, the cap 52 may be coupled to the proximal connector 14 and/or the distal connector 16 via threads or another suitable method. In some embodiments, installing the cap 52 on the proximal connector 14 and/or the distal connector 16 may facilitate protection of the flush device 10 from contaminants and inadvertent use.

Figure 5:
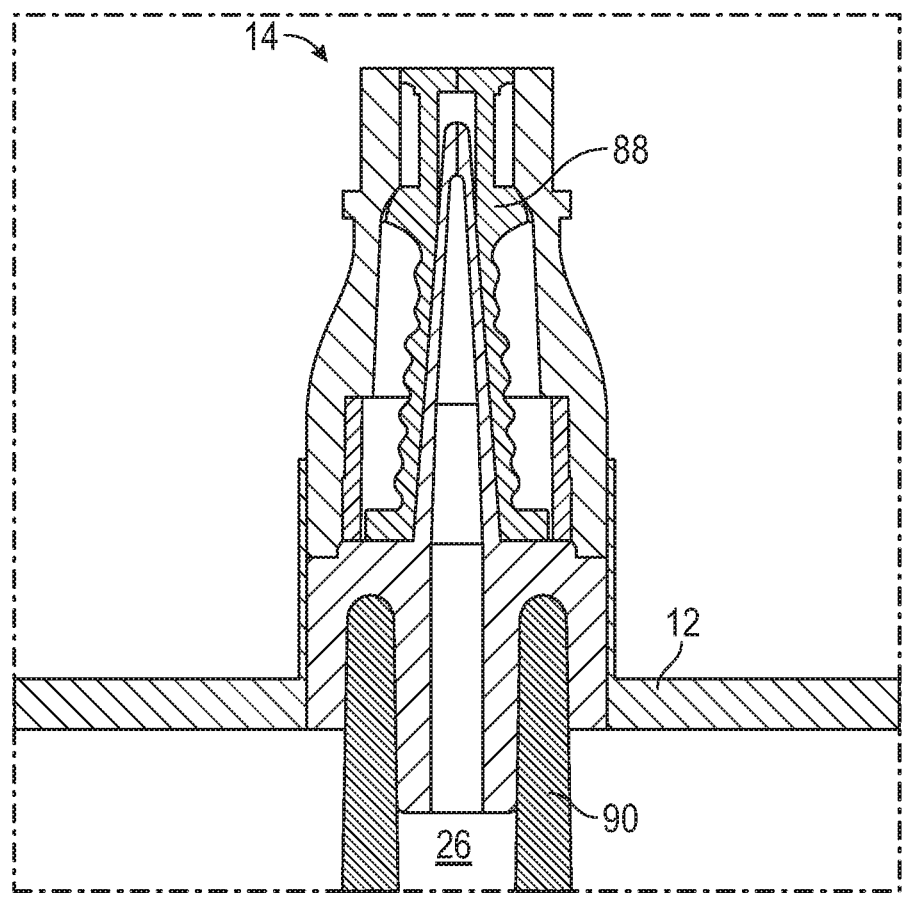
FIG. 5 is a cross-sectional view of an example proximal connector, according to some embodiments.

FIG. 5 illustrates an example needleless connector, according to some embodiments. In some embodiments, the proximal connector 14 may include any suitable needleless connector. The proximal connector 14 may include or correspond to the needleless connector of FIG. 5, according to some embodiments. The needleless connector of FIG. 5 may be described in further detail in U.S. Pat. No. 8,066,670, filed Nov. 5, 2007, entitled "VASCULAR ACCESS DEVICE SEPTUM VENTING," which is hereby incorporated by reference.

In some embodiments, the proximal connector 14 may include a septum 88, which may prevent fluid from exiting the flush device 10. In some embodiments, the proximal connector 14 may be integrally formed with the housing 12. In some embodiments, the proximal connector 14 may be monolithically formed with the housing 12 as a single unit. In some embodiments, the first conduit 26 may include tubing 90, which may be integrated with the proximal connector 14.

All examples and conditional language recited herein are intended for pedagogical objects to aid the reader in understanding the disclosure and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the invention.

The invention claimed is:

1. A medical device for drawing blood through an indwelling catheter and for providing continuous flushing of the indwelling catheter, comprising:
   a housing forming a proximal connector and a distal connector, wherein the distal connector comprises a luer adapter by which an indwelling catheter is coupled to the housing;
   a first conduit disposed within the housing and extending from the proximal connector to the distal connector, the first conduit forming a fluid path for drawing blood via the indwelling catheter using a blood draw device connected to the proximal connector;
   a replaceable fluid reservoir disposed within the housing, the replaceable fluid reservoir containing a flushing fluid;
   a second conduit disposed within the housing and extending between the fluid reservoir and the first conduit, the second conduit forming a fluid path for injecting the flushing fluid into the first conduit and through the distal connector to thereby flush the indwelling catheter;
   a pump disposed within the housing, wherein the pump is configured to continuously pump the flushing fluid from the fluid reservoir through the second conduit, and into the first conduit to thereby continuously flush the indwelling catheter to prevent occlusion of the indwelling catheter;
   a switch disposed on the housing for deactivating the pump while blood is drawn through the first conduit and for reactivating the pump after blood is drawn through the first conduit to resume the continuous flushing of the indwelling catheter; and
   a one-way valve disposed within the second conduit, wherein the one-way valve is configured to prevent blood from flowing beyond the one-way valve toward the fluid reservoir while blood is drawn through the first conduit.

2. The medical device of claim 1, wherein the proximal connector comprises a needleless connector that includes a septum having a slit, and wherein the blood draw device inserts through the slit when coupled to the proximal connector to form the fluid path for drawing blood.

3. The medical device of claim 1, wherein the pump provides a fluid flow rate of 0.2 mL/hr.

4. The medical device of claim 3, wherein the replaceable fluid reservoir contains 5 mL of flushing fluid such that the medical device provides continuous flushing of the indwelling catheter for an entire day without replacing the replaceable fluid reservoir.

5. The medical device of claim 1, wherein the medical device further comprises a clothing article configured to be worn by a patient, wherein the housing is coupled to the clothing article.

6. The medical device of claim 5, wherein the clothing article comprises an arm band.

7. The medical device of claim 1, wherein the first conduit comprises a tubing.

8. The medical device of claim 1, wherein the proximal connector is integrated into a first side of the housing and the distal connector is integrated into a second side of the housing opposite the first side.

9. The medical device of claim 1, wherein the second conduit comprises a tubing.

10. The medical device of claim 9, wherein the pump comprises a peristaltic medical infusion pump having a plurality of members that sequentially push on the tubing.

11. The medical device of claim 1, wherein the replaceable fluid reservoir comprises a syringe.

12. The medical device of claim 1, wherein the replaceable fluid reservoir is a vial.

13. The medical device of claim 1, further comprising:
an indicator integrated into the housing, the indicator identifying a volume of flushing fluid remaining in the replaceable fluid reservoir.

14. The medical device of claim 1, wherein the pump is configured to continuously pump the flushing fluid from the fluid reservoir through the second conduit by periodically pumping a specified amount of the flushing fluid from the fluid reservoir, the specified amount being configured to prevent occlusion of the indwelling catheter.

15. A method for preventing occlusion of an indwelling catheter while allowing blood draws through the indwelling catheter, the method comprising: connecting a medical device to an indwelling catheter, the medical device comprising: a housing forming a proximal connector and a distal connector, wherein the distal connector comprises a luer adapter by which the indwelling catheter is coupled to the housing; a first conduit disposed within the housing and extending from the proximal connector to the distal connector, the first conduit forming a fluid path for drawing blood via the indwelling catheter using a blood draw device connected to the proximal connector; a replaceable fluid reservoir disposed within the housing, the replaceable fluid reservoir containing a flushing fluid; a second conduit disposed within the housing and extending between the fluid reservoir and the first conduit, the second conduit forming a fluid path for injecting the flushing fluid into the first conduit and through the distal connector to thereby flush the indwelling catheter; a pump disposed within the housing, wherein the pump is configured to continuously pump the flushing fluid from the fluid reservoir through the second conduit, and into the first conduit to thereby continuously flush the indwelling catheter to prevent occlusion of the indwelling catheter; a switch disposed on the housing for deactivating the pump while blood is drawn through the first conduit and for reactivating the pump after blood is drawn through the first conduit to resume the continuous flushing of the indwelling catheter; and a one-way check valve disposed within the second conduit, wherein the one-way check valve is configured to prevent blood from flowing beyond the one-way check valve toward the fluid reservoir while blood is drawn through the first conduit; activating the pump to cause the indwelling catheter to be continuously flushed; in conjunction with deactivating the pump, connecting the blood draw device to the proximal connector to draw blood through the first conduit via the indwelling catheter; and after drawing the blood and after disconnecting the blood draw device, reactivating the pump to cause the indwelling catheter to again be continuously flushed.

* * * * *